(12) United States Patent
Hernandez (10) Patent No.: US 7,559,327 B2
(45) Date of Patent: Jul. 14, 2009

(54) VENTILATION INTERFACE

(75) Inventor: Shara Hernandez, Davie, FL (US)

(73) Assignee: Respcare, Inc., Coconut Creek, FL (US)

( * ) Notice: Subject to any disclaimer, the term of this patent is extended or adjusted under 35 U.S.C. 154(b) by 627 days.

(21) Appl. No.: 11/139,496

(22) Filed: May 31, 2005

(65) Prior Publication Data

US 2006/0266361 A1     Nov. 30, 2006

(51) Int. Cl.
*A61M 16/00*     (2006.01)
*A61M 15/08*     (2006.01)
*A61M 16/20*     (2006.01)

(52) U.S. Cl. .......................... 128/207.18; 128/203.22; 128/204.18; 128/205.24; 128/205.25; 128/206.21

(58) Field of Classification Search ............ 128/207.18, 128/200.26, 207.13, 200.24, 204.18, 205.11, 128/205.24, DIG. 26
See application file for complete search history.

(56) References Cited

U.S. PATENT DOCUMENTS

| | | | |
|---|---|---|---|
| 1,125,542 A | | 1/1915 | Humphries |
| 2,693,800 A | * | 11/1954 | Caldwell ............... 128/207.18 |
| 3,670,726 A | | 6/1972 | Mahon et al. |
| 3,739,774 A | | 6/1973 | Gregory |
| 3,754,552 A | | 8/1973 | King |
| 3,861,385 A | | 1/1975 | Carden |
| 3,902,486 A | | 9/1975 | Guichard |
| 3,905,361 A | | 9/1975 | Hewson et al. |
| 4,156,426 A | | 5/1979 | Gold |
| 4,267,845 A | | 5/1981 | Robertson, Jr. et al. |
| 4,273,124 A | | 6/1981 | Zimmerman |
| 4,312,359 A | | 1/1982 | Olson |
| 4,367,735 A | | 1/1983 | Dali |
| 4,367,816 A | | 1/1983 | Wilkes |
| 4,406,283 A | | 9/1983 | Bir |
| 4,422,456 A | | 12/1983 | Teip |
| 4,493,614 A | | 1/1985 | Chu et al. |
| 4,549,542 A | | 10/1985 | Chien |
| 4,587,967 A | | 5/1986 | Chu et al. |

(Continued)

FOREIGN PATENT DOCUMENTS

DE         146688         2/1981

(Continued)

OTHER PUBLICATIONS

Snapp Nasal Interface, Tiara Medical Systems, Inc. http://www.tiaramed.com/asp_shop/shopdisplayproducts.asp?id=109&cat=SNAPP%2A+Nasal+Interface, viewed May 17, 2005.

(Continued)

*Primary Examiner*—Justine R Yu
*Assistant Examiner*—Clinton Ostrup
(74) *Attorney, Agent, or Firm*—Maier & Maier, PLLC (57) ABSTRACT

A ventilation interface device is disclosed that may include a hollow cannula, at least one nasal insert and at least one exhaust port or may include a mask designed to cover a user's nose, mouth or both nose and mouth. The at least one nasal insert may be formed so as to fit in any size nares of any user and may be detachable. Additionally, the at least one exhaust port may be in any of a variety of orientations and, in some embodiments, contain sealable ports.

20 Claims, 5 Drawing Sheets

U.S. PATENT DOCUMENTS

| | | | |
|---|---|---|---|
| 4,601,465 | A | 7/1986 | Roy |
| 4,617,637 | A | 10/1986 | Chu et al. |
| 4,660,555 | A | 4/1987 | Payton |
| 4,699,139 | A | 10/1987 | Marshall et al. |
| 4,706,664 | A | 11/1987 | Snook et al. |
| 4,753,233 | A | 6/1988 | Grimes |
| 4,774,946 | A | 10/1988 | Ackerman et al. |
| 4,899,740 | A | 2/1990 | Napolitano |
| 4,915,105 | A | 4/1990 | Lee |
| 4,996,983 | A | 3/1991 | AmRhein |
| 5,000,173 | A | 3/1991 | Zalkin et al. |
| 5,022,900 | A | 6/1991 | Bar-Yona et al. |
| 5,025,805 | A | 6/1991 | Nutter |
| 5,038,772 | A | 8/1991 | Kolbe et al. |
| 5,046,491 | A | 9/1991 | Derrick |
| 5,074,297 | A | 12/1991 | Venegas |
| 5,113,857 | A | 5/1992 | Dickerman et al. |
| 5,121,745 | A | 6/1992 | Isreal |
| 5,127,397 | A | 7/1992 | Kohnke |
| 5,137,017 | A | 8/1992 | Salter |
| D333,015 | S | 2/1993 | Farmer et al. |
| 5,188,101 | A | 2/1993 | Tumolo |
| 5,265,592 | A | 11/1993 | Beaussant |
| 5,265,595 | A | 11/1993 | Rudolph |
| 5,269,296 | A | 12/1993 | Landis |
| 5,271,391 | A | 12/1993 | Graves |
| 5,299,599 | A | 4/1994 | Farmer et al. |
| 5,335,656 | A | 8/1994 | Bowe et al. |
| 5,355,893 | A | 10/1994 | Mick et al. |
| 5,372,130 | A | 12/1994 | Stern et al. |
| 5,375,593 | A | 12/1994 | Press |
| 5,385,141 | A | 1/1995 | Granatiero |
| 5,394,568 | A | 3/1995 | Brostrom et al. |
| 5,396,885 | A | 3/1995 | Nelson |
| 5,398,676 | A | 3/1995 | Press et al. |
| 5,400,776 | A | 3/1995 | Bartholomew |
| 5,425,359 | A | 6/1995 | Liou |
| 5,437,267 | A | 8/1995 | Weinstein et al. |
| 5,509,409 | A | 4/1996 | Weatherholt |
| 5,526,806 | A | 6/1996 | Sansoni |
| 5,533,506 | A | 7/1996 | Wood |
| 5,560,354 | A | 10/1996 | Berthon-Jones et al. |
| 5,682,881 | A | 11/1997 | Winthrop et al. |
| 5,740,799 | A | 4/1998 | Nielsen |
| 5,794,619 | A | 8/1998 | Edelman et al. |
| 5,906,203 | A | 5/1999 | Klockseth et al. |
| 5,954,049 | A | 9/1999 | Foley et al. |
| 6,123,071 | A | 9/2000 | Berthon-Jones et al. |
| 6,357,441 | B1 | 3/2002 | Kwok et al. |
| 6,431,172 | B1 | 8/2002 | Bordewick |
| 6,439,234 | B1 | 8/2002 | Curti et al. |
| 6,478,026 | B1 | 11/2002 | Wood |
| 6,561,188 | B1 | 5/2003 | Ellis |
| 6,561,193 | B1 | 5/2003 | Noble |
| 6,571,798 | B1 | 6/2003 | Thornton |
| 6,581,602 | B2 | 6/2003 | Kwok et al. |
| 6,595,214 | B1 | 7/2003 | Hecker et al. |
| 6,595,215 | B2 | 7/2003 | Wood |
| 6,637,434 | B2 | 10/2003 | Noble |
| 6,655,385 | B1 | 12/2003 | Curti et al. |
| 6,679,265 | B2 | 1/2004 | Strickland et al. |
| 6,766,800 | B2 | 7/2004 | Chu et al. |
| 2002/0046755 | A1 | 4/2002 | DeVoss |
| 2002/0124849 | A1 | 9/2002 | Billette De Villemeur |
| 2003/0079749 | A1 | 5/2003 | Strickland et al. |
| 2003/0196658 | A1 | 10/2003 | Ging et al. |
| 2004/0016432 | A1* | 1/2004 | Genger et al. ......... 128/204.18 |
| 2004/0112384 | A1 | 6/2004 | Lithgow et al. |
| 2005/0028822 | A1 | 2/2005 | Sleeper et al. |
| 2005/0033247 | A1 | 2/2005 | Thompson |
| 2005/0051176 | A1 | 3/2005 | Riggins |
| 2005/0061326 | A1 | 3/2005 | Payne, Jr. |
| 2005/0133039 | A1* | 6/2005 | Wood ................. 128/207.18 |
| 2005/0235999 | A1* | 10/2005 | Wood et al. .......... 128/207.18 |

FOREIGN PATENT DOCUMENTS

| | | |
|---|---|---|
| DE | 19944242 | 3/1991 |
| DE | 3719009 | 12/1998 |
| EP | 0658356 | 6/1995 |
| GB | 0532214 | 1/1941 |
| GB | 2368533 | 5/2002 |
| GB | 2385533 | 8/2003 |
| WO | WO 01/97892 A1 | 12/2001 |
| WO | PCT/AU2004/001832 | 7/2005 |

OTHER PUBLICATIONS

ComfortCurve Nasal Interface, Respironics, Inc. http://www.cpap.com/productpage/1842, viewed May 31, 2005.

Respironics Co.—Mask Family—http://masksfamily.respironics.com/ viewed on Jul. 24, 2006.

ResMed Co.—Mask Products—http://resmed.com/portal/site/ResMedUS/index.jsp?front_door=true viewed on Jul. 24, 2006.

Fisher and Paykel Co.—Product Family—http://www.fphcare.com/osa/products.asp viewed on Jul. 24, 2006.

Hans Rudoply Inc.—Mask Products—http://www.rudolphkc.com/products.php?category=MASKS viewed on Jul. 24, 2006.

Snapp Nasal Interface, Tiara Medical Systems, Inc. http://www.tiaramed.com/asp_shop/shopdisplayproducts.asp?id=109&cat=SNAPP%2A+Nasal+Interface viewed on Jul. 24, 2006.

* cited by examiner

VENTILATION INTERFACE

BACKGROUND OF THE INVENTION

1. Field of the Invention

The present invention relates to ventilation devices, and particularly to both ventilation devices having a nasal inserts and exhalation ports, and mask type ventilation devices, each having particular utility in various modes of therapy for obstructive sleep apnea as well as utility for continuous positive airway pressure (CPAP) devices, bi-level positive airway pressure (BiPAP) devices and non-invasive ventilation.

2. Description of the Related Art

Pressurized gas and ventilation devices designed to be worn on a user's head or face are utilized for a variety of purposes. These devices may be used to provide relief from respiratory ailments, such as sleep apnea, provide a conduit for aerosolized medicine, or non-invasively provide a user with an appropriate amount of gas, such as oxygen. These devices, however, can be disruptive to an activity the wearer seeks to perform and may be generally uncomfortable to the wearer. Additional problems arise with these devices because gas flow inside the mask or cannula is not optimized and may cause irritations associated with improper gas flow, such as excess noise.

The treatment of sleep apnea is a known field of use for pressurized gas devices. Sleep apnea is a potentially lethal affliction in which breathing stops recurrently during sleep. Sleep apnea may be of the obstructive type (sometimes known as the pickwickian syndrome) in which the upper airway is blocked in spite of airflow drive; the central type with decreased respiratory drive; or a mixed type. Breathing may cease for periods long enough to cause or to exacerbate cardiac conditions, and may be accompanied by swallowing of the tongue. Sleep apnea frequently results in-fitful periods of both day and night sleeping with drowsiness and exhaustion, leaving the patient physically and mentally debilitated.

In recent years it has been found that various forms of positive airway pressure during sleep can be an effective form of therapy for the apnea sufferer. Ventilation can be applied in the form of Continuous Positive Airway Pressure (CPAP) in which a positive pressure is maintained in the airway throughout the respiratory cycle, Bilevel Positive Airway Pressure (BiPAP) in which positive pressure is maintained during inspiration but reduced during expiration, and Intermittent Mechanical Positive Pressure Ventilation in which pressure is applied when an episode of apnea is sensed. Positive airway pressure devices have traditionally employed either a face mask which only covers the patient's nose, or nasal pillows as the interface between the ventilation device and the patient's airway. However, there are problems with both of these interfaces.

The face mask requires a harness, headband, or other headgear to keep the mask in position, which many patient's find uncomfortable, particularly when sleeping. The face mask must seal the mask against the patient's face, and may cause irritation and facial sores, particularly if the patient moves his head while sleeping, causing the mask to rub against the skin. Face masks are also position dependent, and may leak if the mask changes position with movement of the patient's head. The face mask applies pressure to the sinus area of the face adjacent to the nose, causing the airways to narrow, thereby increasing the velocity of flow through the airway, but decreasing the pressure against the nasal mucosal walls. This strips moisture from the mucosal wall during inspiration, thereby causing drying and a burning sensation. These factors will often result in the patient's removal of the mask and discontinuance of positive airway pressure therapy.

Nasal pillows are pillowed style nasal seals which are pressed against the inferior portion of the nares to close the nostril openings. Nasal pillows require a headband or harness to maintain the pressure, resulting in the same patient discomfort noted with face masks. Nasal pillows have about a 0.25" internal diameter at the nasal entry port where the seal is made. Therefore, pressurized air must pass through a constricted port, increasing the velocity of airflow, with resultant drying and burning of the nasal airways. The narrowed interface diameter of the nasal pillows causes a pressure drop, which is directly proportional to the drop in the number of available air molecules within the closed system. It is the volume of air molecules at the area in the patient's throat where the apneic events appear that is needed to correct apnea. The narrower the airways or the internal diameter of the nasal interface, the lower the volume of air molecules that will be available and the greater the driving pressure that is required to meet the volume demand. An increase in driving pressure does not fully compensate for the loss in the number of air molecules available.

A further problem with existing ventilation devices is that the carbon dioxide bleed ports for venting exhaled gases are noisy on both nasal face masks and nasal pillows. The whistling noise that occurs while utilizing such devices can prove quite annoying to the patient, awakening the patient and causing the patient to discontinue use of the ventilation device.

Another problem associated with the carbon dioxide bleed ports is a lack of alternative sizes and shapes of bleed ports which may be necessary for a certain application or for the specific needs of a patient. Past examples of bleed ports have used only fixed-size singular bleed port or pairs of bleed ports that do not provide for the efficient and quiet exhaustion of gases, resulting in inefficient use and uncomfortable wearing by the user.

Previous mask-type devices, such as face masks, ventilators and ventilation masks, have also utilized bleed ports. These devices, which may fit over a user's mouth and nose or only a user's nose, typically have either a single port or a pair of ports on the mask. However, with these masks, the exhaled gases can create a significant amount of noise during the exhaustion or exhalation process, disturbing the user and potentially interrupting use of the device. Additionally, the location, size and amount of exhaust ports on standard mask-type ventilation devices do not allow for optimal exhaust gas flow in certain situations, nor do they allow for adjustments to be made to suit a particular patient's needs or requirements.

A number of devices have been proposed which include a ventilation interface for supplying gases to be inhaled, for collecting exhaled gases, or for mounting sensors for measuring or monitoring respiratory function.

U.S. Pat. Nos. 5,335,654 and 5,535,739, issued on Aug. 9, 1994 to Rapoport and Jul. 16, 1996 is to Rapoport et al., respectively, describe a CPAP system using a conventional nasal mask, the innovation comprising a flow sensor in the input line connected to a signal processor to determine the waveform of airflow, which is connected to a flow controller to adjust the pressure of airflow as required. U.S. Des. Pat. No. 333,015, issued Feb. 2, 1993 to Farmer et al. shows an ornamental design for a nasal mask. U.S. Des. No. 262,322, issued Dec. 15, 1981 to Mizerak, shows an ornamental design for a nasal cannula with a mouth mask.

U.S. Pat. No. 4,782,832, issued Nov. 8, 1988 to Trimble et al., discloses nasal pillows held in the patient's nose by a harness arrangement, the device having a plenum with two accordion or bellows shaped nipples for fitting against the nostril openings. U.S. Pat. No. 4,774,946, issued Oct. 4, 1988 to Ackerman et al., teaches a nasal and endotracheal tube apparatus for administering CPAP to infants, the nose tubes having a bulbous portion for seating in the pares of an infant and a headband with a VELCRO®, or substantially similar hook and loop fastener, closure for supporting the cannula and supply tubes.

U.S. Pat. Nos. 5,269,296, issued to Landis on Dec. 14, 1993, and U.S. Pat. Nos. 5,477,852 and 5,687,715, issued to Landis et al. on Dec. 26, 1995, and Nov. 18, 1997, respectively, describe CPAP devices for the treatment of sleep apnea with relatively stiff or rigid nasal cannulae or prongs surrounded by inflatable cuffs to retain the cannulae in the pares, but which also may be supplemented by an inflatable head harness to position the cannulae and hold them in place, the two cannulae being joined by a conduit having vent holes to vent exhaled air. U.S. Pat. No. 5,533,506, issued Jul. 9, 1996 to the present inventor, discloses a nasal tube: assembly in which the tubes are tapered, frustro-conical assemblies with a soft membrane over the distal tip and a washer at the base of the nasal tube to prevent the tubes from falling through a support bar connected to a harness, the nasal tubes forming a positive seal with the inside of the nostrils to prevent the escape of gases.

U.S. Pat. No. 5,682,881, issued Nov. 4, 1997 to Winthrop et al., shows a nasal cannula for CPAP therapy with cone shaped nasal prongs in which the cannula is secured to the patient's upper lip by adhesive tape strips. U.S. Pat. No. 4,915,105, issued Apr. 10, 1990 to Lee, teaches a miniature respiratory breather apparatus in which relatively stiff or rigid nasal tubes have elastomeric packings for sealing the tubes in the nares.

U.S. Pat. No. 5,429,125, issued Jul. 4, 1995 to Wagner et al., teaches a mask-style ventilation device for providing oxygen to a user in which there are no exhaust or exhalation ports. U.S. Pat. No. 5,586,551, issued Dec. 24, 1996 to Hilliard, teaches a mask-style ventilation device for providing oxygen and other gases to a user in which there are two fixed size exhaust ports.

None of the above inventions and patents, taken either singly or in combination, is seen to describe the instant invention as claimed. Thus a ventilation interface solving the aforementioned problems is desired.

SUMMARY OF EXEMPLARY EMBODIMENTS OF THE INVENTION

In an exemplary embodiment of the invention, a conventional ventilation interface for the application of positive air pressures is coupled with a variety of different styles of nasal inserts and a variety of different styles of exhaust ports. The nasal inserts may be formed in a one-size fits all style and may be retained in the nares of a user through friction or lateral pressure of gas flow. Additionally, the ventilation interface may have one or more exhaust ports disposed on the bottom of the interface, and the one or more exhaust ports may have adjustable apertures.

In another embodiment of the invention, a ventilation interface comprising a hollow cannula and having a pair of nasal inserts is again disclosed. The bottom wall of the cannula, however, may contain only one exhaust port or a series of exhaust ports. The exhaust ports may have an adjustable flow rate.

In another embodiment of the invention, the nasal inserts disposed on an upper wall of a cannula may be formed so as to have a bottom diameter that is larger than a top diameter and a central diameter that is smaller than both the top and bottom diameters. Additionally, the cannula may contain sealable exhaust ports proximal the distal ends of the cannula. Further, a series of exhaust ports may be disposed on the bottom wall of the cannula that may be sealed by the user.

In a different embodiment of the invention, at least one exhaust port may be disposed on a face mask or ventilation mask. The at least one exhaust port may be any of a variety of sizes and may optionally be adjustable in size or number. Further, the at least one exhaust port may be sealed to prevent exhaust gas flow from those ports.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Advantages of embodiments of the present invention will be apparent from the following detailed description of the preferred embodiments thereof, which description should be considered in conjunction with the accompanying drawings in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description, discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or more of operation.

Referring now to the drawings, wherein like reference numerals designate identical or corresponding parts throughout the several views.

Referring generally to FIGS. 1-10 and 13, a ventilation interface with at least one nasal insert and at least one exhaust port is shown. The cannula may be made out of any suitable material, for example, silicone. The cannula may also be one of a variety of sizes, dependent on the user or application, and can also be fashioned in a one-size-fits-all manner. The at least one nasal insert can be formed and shaped in any of a variety of manners. Further, in any of the embodiments, an airtight seal may be formed between the at least one nasal insert and the nares of the user, preventing a loss of the gas, aerosol or medication being delivered. The gas, aerosol or medication may be delivered to the device through delivery tubes that may be attached to the distal ends of the cannula.

Figure 11:
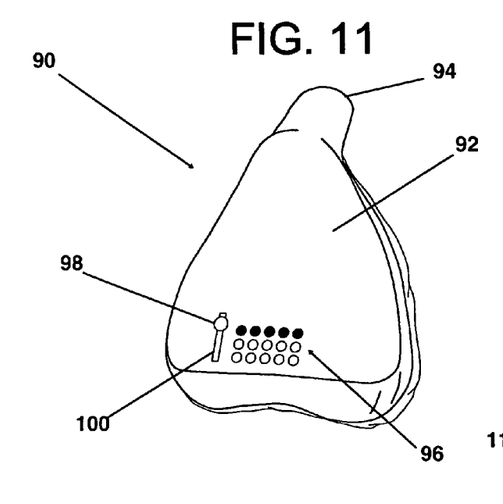
FIG. 11 illustrates another exemplary embodiment of the present invention, showing adjustable exhaust ports on a ventilation mask.
Figure 12:
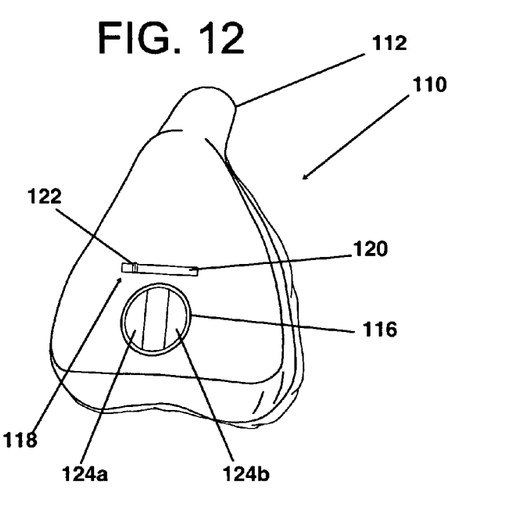
FIG. 12 illustrates another exemplary embodiment of the present invention, showing an exhaust port with an adjustable aperture on a ventilation mask.

Referring generally to FIGS. 11-12, ventilation interface having the form of a mask with at least one input and at least one exhaust port is shown. The interface may be made out of any suitable material and may incorporate a variety of materials to, for example, provide padding on the interface. The interface may have an airtight seal with the face of a user and gas, aerosol or any type of medication may be delivered to the device through delivery tubes that may be attached to the at least one input.

In further embodiment of the present invention, a variety of different exhaust ports may be disposed on the ventilation interface. There may be a single port or a plurality of ports. The single port or each of the plurality of ports may be coupled to a mechanism for altering the open area of the aperture or, alternatively, may include a plug or plugs for altering the open area of the aperture. In a further embodiment of the invention, the exhaust ports may be disposed in a variety of different locations on the cannula.

Figure 1:
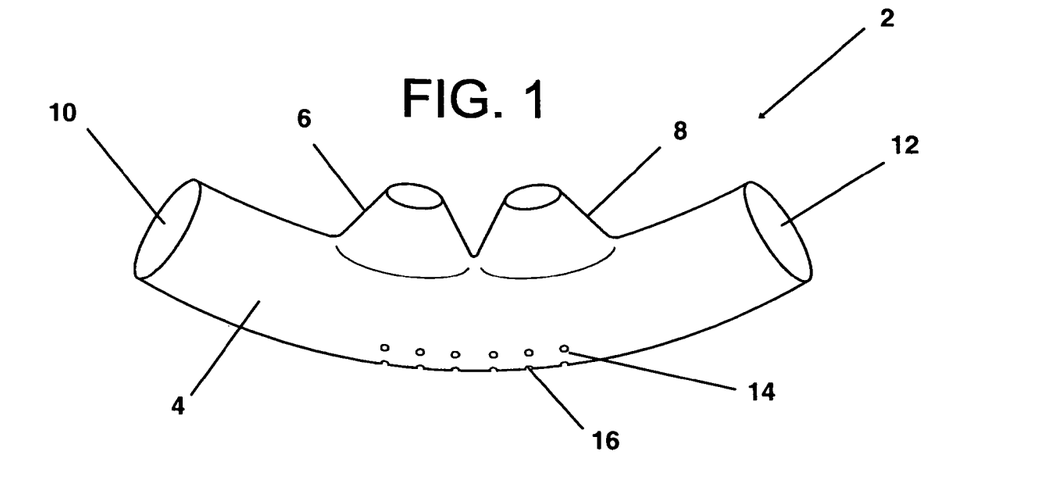
FIG. 1 illustrates a side view of an exemplary embodiment of the present invention showing volcano-shaped nasal inserts and a series of exhaust ports.

Specifically referring to FIG. 1, an exemplary embodiment of the invention is shown. In this exemplary embodiment a nasal interface device 2 has two volcano-shaped nasal inserts 6 and 8 that are disposed on a cannula 4. The volcano-shaped inserts 6 and 8 feature a circular base that may taper in size from the base to a distal end. The inserts may be formed in a one-size-fits-all fashion or any size desired for a particular application. The distal end of the nasal insert is disposed in such a manner as to be inserted into the nares of a user. Air or any other type of gas as well as any aerosol or medication may then flow through the cannula and through the nasal inserts. In another embodiment of the invention, the inserts may be removable and replaceable with different size inserts.

Still referring to FIG. 1, a plurality of holes 14 may be linearly disposed on the cannula on a side approximately opposite to the nasal inserts. The holes 14 may act as exhaust ports insofar as they can allow for the exhaustion of gas or aerosol through cannula 4 and into the nares of the user while also allowing for the expulsion of unwanted gases. Each hole, e.g. 16, may be of any shape, for example circular, substantially circular or oval. In one embodiment the plurality of holes 14 may be disposed in a series of parallel lines or, alternatively, in any pattern desired.

Additionally, in FIG. 1, the distal ends 10 and 12 of the cannula may optionally be oriented in an upward fashion or in such a manner so as to substantially contour to the face of a user. These different orientations of the distal ends 10 and 12 of the cannula are illustrated in other exemplary embodiments and can allow for different gas flow dynamics. Additionally, orienting the distal ends 10 and 12 of cannula 4 in different manners may allow for the apparatus to be worn or fastened to the user in variety of manners. Also, any of a variety of different methods of wearing and fastening the device to a user may be implemented. For example, two eye-loops may be disposed towards the tops of the distal ends of cannula 4. In another embodiment, loops may be fitted around distal ends of cannula 4 using friction or any other type of adhesion in order to attach straps or other types of apparatus that may be worn by a user.

Figure 2:
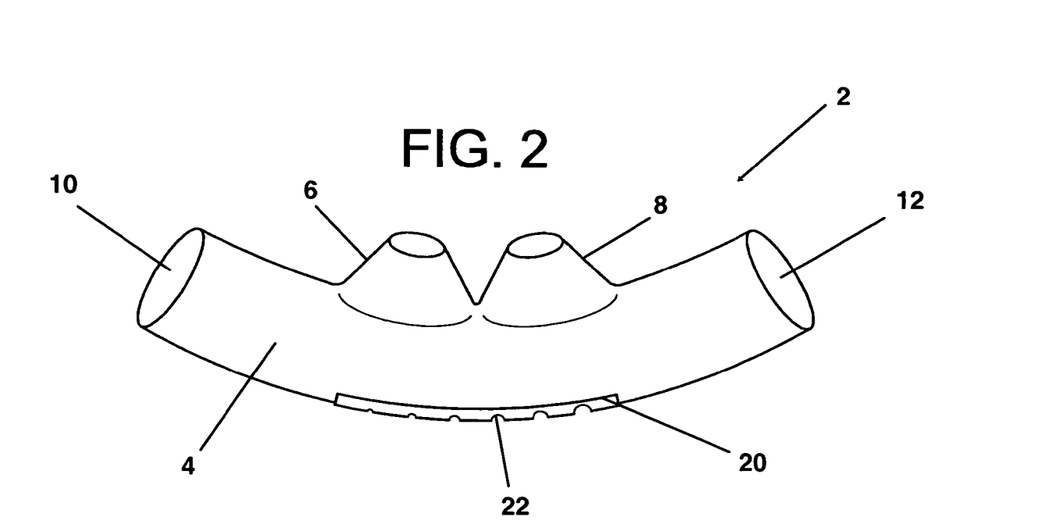
FIG. 2 illustrates another side view of an exemplary embodiment of the present invention showing a sliding exhaust port cover.

Referring now to FIG. 2, another exemplary embodiment of the present invention is shown. In this embodiment, cannula 4 is shown with slider 20 comprising a series of different sized openings is disposed substantially linearly on a portion of the cannula approximately opposite to the nasal inserts 6 and 8. In this embodiment, a single exhaust port of a predetermined size may be disposed beneath slider 20. This exhaust port may be substantially circular, oval, or any other shape desired. The openings on slider 20 may be approximately of the same shape as the single exhaust port on the cannula, or any other shape allowing exhaust gas to pass through the openings. Slider 20 may then be moved, for example, laterally, to position one of the openings in the slider over the exhaust port on the cannula, thus varying the effective cross section of the exhaust port.

The exhaust port may be adjusted in this or any of a number of different exemplary embodiments in order to vary the exhaust gas flow from the device. It may be desired to adjust the exhaust gas flow in the ventilation interface for a variety of reasons. In one exemplary embodiment, the exhaust gas flow may be adjusted to improve gas or aerosol circulation inside the ventilation interface. In another exemplary embodiment, the exhaust gas flow may be adjusted to eliminate undesired noise resulting from gas exiting a differently adjusted exhaust port or series of exhaust ports.

In the exemplary embodiment shown in FIG. 2, opening 22 is shown as being disposed over an opening in the bottom of cannula 4. Therefore, in this embodiment, exhaust gas may exit cannula 4 via opening 22, or a user may laterally move slider 20 to position any of the other openings over the exhaust port in order to change the exhaust flow rate and characteristics.

Figure 3:
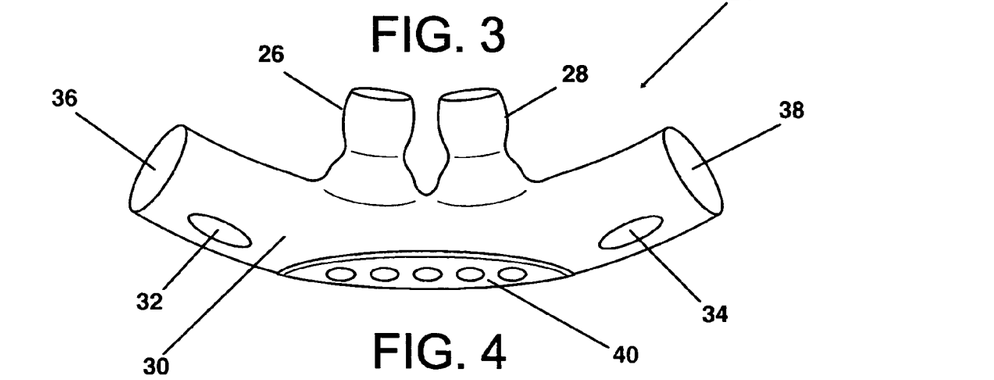
FIG. 3 illustrates another side view of another exemplary embodiment of the present invention showing a variety of exhaust ports.

Referring now to FIG. 3, another exemplary embodiment of the invention is shown. In this embodiment, two nasal inserts (26 and 28) are again disposed on a nasal interface 24. Nasal inserts 26 and 28 in FIG. 3 may have a substantially circular or oval base and substantially circular, oval or nostril-shaped distal ends. Further, nasal inserts 26 and 28 may also have an indented portion approximately between the base and the distal end of the nasal insert. Additionally, nasal inserts 28 and 28 may be formed in a variety of sizes and shapes. For example, the nasal inserts may have bodies that taper into distal ends that are round, oval, or shaped like the inside of a nose. Also, in any of the embodiments, the nasal inserts may be fashioned in a one-size-fits-all manner.

In a further embodiment, nasal inserts 26 and 28 of FIG. 3 may be removable and replaceable with other nasal inserts. In this embodiment, nasal inserts 26 and 28 may be removable in a twist-off manner, similar, for example, to the removal of a nipple from a baby bottle. In this embodiment, the nasal inserts could have a first flange or lip portion on the lower portion of the removable nasal insert and a second flange or lip portion on the bottom of the nasal inserts. Thus, the nasal inserts could be removed and replaced with another pair of nasal inserts that could be fastenably attached to cannula 30. Alternatively, nasal inserts 26 and 28 may have a screw-like threading, allowing them to be screwed into cannula 4.

Further, the cannula 30 in FIG. 3 may contain exhaust ports 32 and 34 proximate each distal end 36 and 38 of cannula 30. These exhaust ports 32 and 34 may be of any shape, such as oval or substantially circular, and may optionally be sealed through use of a plug or any other sealing mechanism. The plug or sealing mechanism may be formed in the shape of the exhaust port and fastenably attached so as to prevent any gas from exiting cannula 30 through the ports.

Additionally, in FIG. 3, a series of exhaust ports 40 of any shape may be disposed on the cannula approximately opposite to the nasal inserts. These exhaust ports 40 may be formed in any shape, for example, circular or oval. This series of exhaust ports 40 may have an additional covering, door or slide which acts to open and close, thus optionally covering the series of exhaust ports. The door or covering may also be used to optionally vary the amount of exhaust gas. In order to more efficiently seal the series of exhaust ports 40, the door or cover may contain a series of tabs that are substantially the same shape as the series of exhaust ports and may be inserted into the series of exhaust ports.

Figure 4:
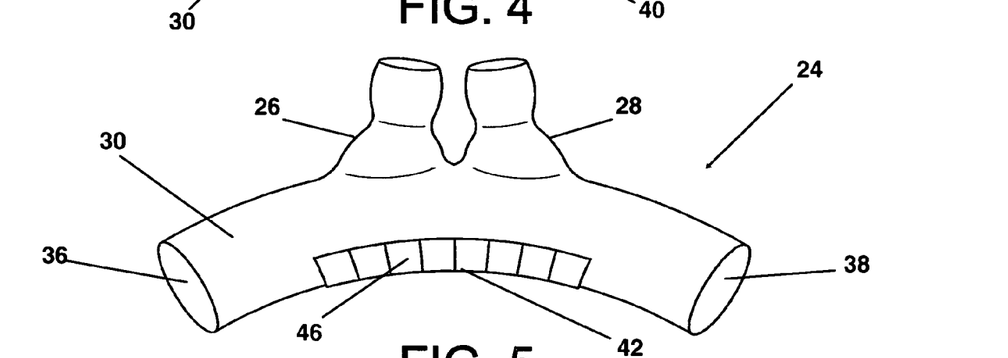
FIG. 4 illustrates another side view of another exemplary embodiment of the present invention showing a sealable series of nasal inserts
Figures 5, 6:
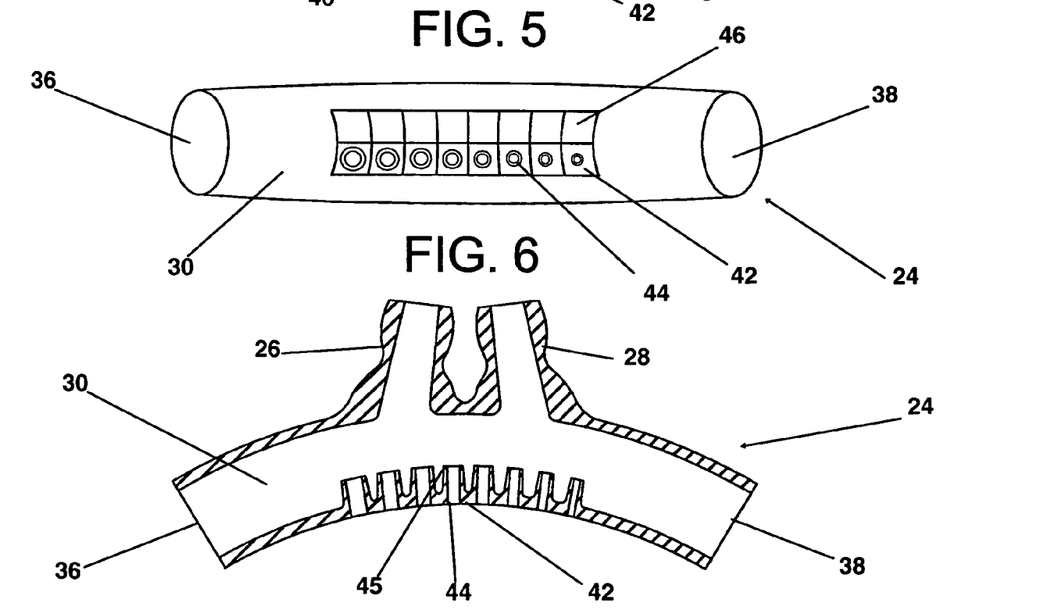
FIG. 5 illustrates a rotated view of the embodiment shown in FIG. 4.
FIG. 6 illustrates a cutaway view of the embodiment shown in FIG. 4.

Referring now to FIGS. 4-6, another embodiment of a nasal interface 24 is shown. FIG. 4 shows an exemplary side view of this embodiment, FIG. 5 shows a rotated bottom view of this embodiment and FIG. 6 shows a cutaway view of this embodiment. Specifically, in this embodiment a pair of nasal inserts 26 and 28 is again shown as disposed on cannula 30. This embodiment further shows a series of exhaust ports 42 disposed on cannula 30. The exhaust ports 42 may be any of a variety of shapes, for example, circular or oval. Additionally, each individual opening 44 (e.g.) may have an associated cover or slider 46 (e.g.) which may act to slide or cover the port 44, thus sealing it and varying the amount of open exhaust gas ports as well as the amount of exhaust gas allowed. Alternatively, appropriately-sized plugs may be used to seal each hole, allowing for the variation of the amount of open exhaust gas ports as well as the amount of exhaust gas allowed.

Further, in the cutaway shown in FIG. 6, interior portions 45 are shown as being disposed inside cannula 30 and as being axially aligned with each opening 44. Interior portions 45 may act to properly direct both gas flow entering the device through distal ends as well as direct exhaust gas In a further exemplary embodiment of the invention, cannula 30 may be disposed so as to curve around the face of the user. In this embodiment, which may create a better fit for some users, distal ends 36 and 38 of cannula 30 may be oriented in such as fashion as to contour to the curvature of, for example, a human face. In this exemplary embodiment, nasal inserts 26 and 28 would remain in the same position as shown in FIGS. 4 and 6. Additionally, exhaust ports 42 may remain in substantially the same position as shown in FIGS. 4 and 6.

Figure 7:
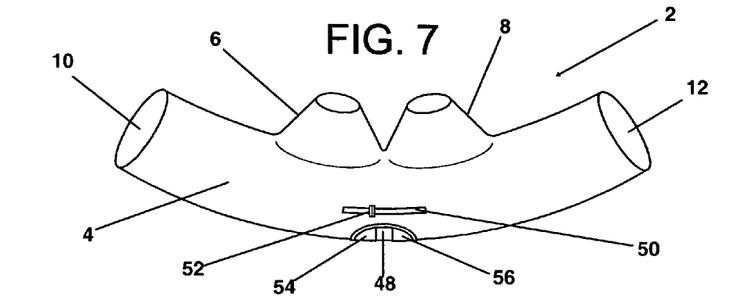
FIG. 7 illustrates another exemplary embodiment of the present invention, showing a sealable aperture.
Figure 8:
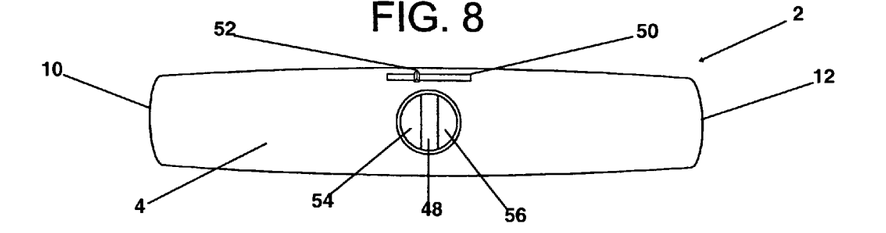
FIG. 8 illustrates a rotated view of the embodiment shown in FIG. 7.

In another embodiment of the invention, as shown in FIGS. 7 and 8, a nasal interface 2 is again depicted. This embodiment again includes nasal inserts 6 and 8 disposed on cannula 4. However, in this embodiment, an aperture 48 is disposed on the lower wall of cannula 4, substantially opposite nasal inserts 6 and 8. Aperture 48 may be disposed over a singular exhaust port or hole on the bottom wall of cannula 4, substantially opposite nasal inserts 6 and 8. Exhaust gases leaving cannula 4 may be channeled through aperture 48 before leaving nasal interface 2. Aperture 48 may be adjusted by a user so as to vary the amount of exhaust gas leaving nasal interface 2. Slide 50 and tab 52 are positioned approximately adjacent aperture 48. In one embodiment, the user may, for example, move tab 52 in slide 50 vertically in order to increase or decrease the effective opening of aperture 48. For example, when tab 52 is in the uppermost or vertical-most position in slide 50, aperture 48 is fully open. The user may however move tab 52 down or south in slide 50. This downward movement causes walls 54 and 56 to move and narrow the opening of aperture 48. Moving tab 52 to the southern-most position of slide 50 will cause walls 54 and 56 to completely seal aperture 48. However, the user may move tab 52 to any position necessary or desired in order to get the proper exhaust gas flow through the ventilation interface. In a further embodiment of the invention, movement of tab 52 may cause aperture 48 to have a decreased diameter as the sides of aperture 48 would close in a circular fashion. Thus as a user moved tab 52 downward would effectively cause a decrease in the diameter of the aperture. This would allow a user to further adjust the characteristics of exhaust flow from the device. In a further embodiment of the invention, aperture 48 may be removed to reveal a single exhaust port, which may be any of a variety of sizes and shapes. In yet a further embodiment of the invention, aperture 48 may be removed and replaced with a different aperture. The different aperture may have a different initial diameter or flow area than that of the initially attached aperture, thus giving the user more exhaust gas flow options. In a further embodiment of the invention, aperture 48 may be removed to reveal a single exhaust port, which may be any of a variety of sizes and shapes.

Figure 9:
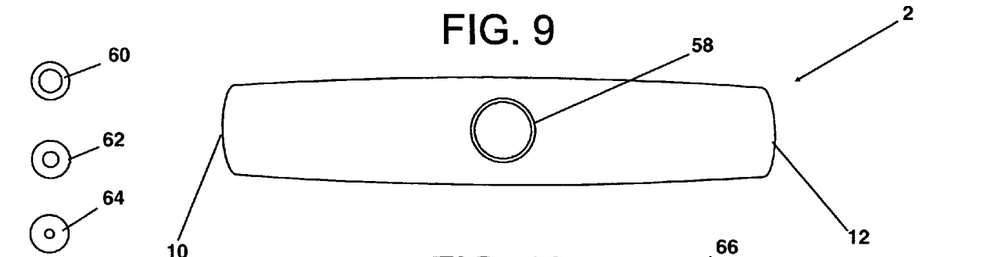
FIG. 9 illustrates another exemplary embodiment of the present invention, showing an exhaust port with different flow settings.

In another embodiment of the invention as shown in FIG. 9, an exhaust port 58 may again be disposed on cannula 4 substantially opposite the nasal inserts 6 and 8. In this embodiment, the exhaust port 58 may be any of a variety of sizes, such as a circle having a diameter of 8-10 mm. In this embodiment, the exhaust port 58 may be left open, allowing a maximum amount of exhaust gas to leave the nasal interface. However, plugs may also be included with the device in order to adjust the rate of exhaust flow. In one embodiment, a variety of plugs (as shown in FIG. 9) may be associated with the nasal interface 2. Each plug may be generally donut-shaped and is designed to fit into the exhaust port. For example, there may be a variety of different plugs, such as plug 60 plug 62 and plug 64, each having a different internal, open diameter. In one embodiment, The ventilation interface may have a plug with a 6 mm diameter (60), a 4 mm diameter (62) and a 2 mm diameter (64). In this embodiment, the different plugs may be interchanged to allow for the proper exhaust flow amount, as dictated by, for example, a doctor's prescription. Additionally, a user could interchange the plugs if they desired to have a different exhaust gas flow, exhaust gas noise or to otherwise alter the exhaust gas flow characteristics. In another embodiment of the invention, the exhaust port may be sealed completely and other exhaust ports, for example exhaust ports near the distal ends of the cannula as in FIG. 3 may be utilized.

Figure 10:
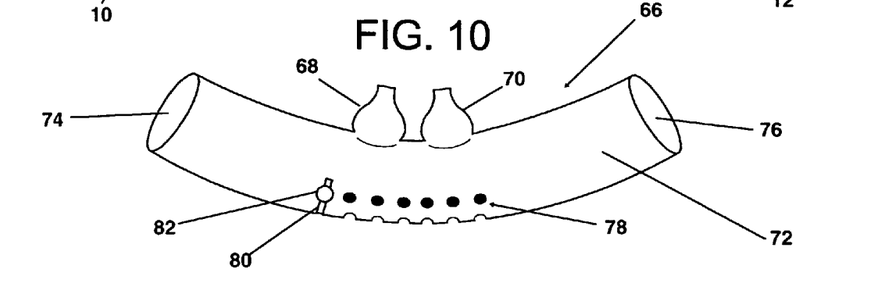
FIG. 10 illustrates another exemplary embodiment of the present invention, showing a series of sealable exhaust ports.

In a another embodiment of the invention shown in FIG. 10, a series of exhaust ports 78, similar those shown in FIG. 1, may again be disposed on a bottom portion of cannula 72 on nasal interface 66, substantially opposite nasal inserts 68 and 70. In this exemplary embodiment, three rows of six holes, which may be circular, substantially circular, oval, or any other shape, are disposed substantially opposite nasal inserts 68 and 70. Additionally, a slide 80 is proximal to the series of holes 78. Slide 80 may be located anywhere on cannula 72; however, in this exemplary embodiment, slide 80 is located to the left of the holes. Included in slide 80 may be tab or switch 82 that may move vertically or horizontally, depending on the orientation of the slide. When moved, tab or switch 82 actuates a cover housed in cannula 72. The actuation of cover causes it to slide in such a manner as to cover and seal the series of holes 78 disposed on the bottom of cannula 72, thus preventing exhaust gas from exiting through those holes. The tab or switch 82 may be positioned in any of a number of positions, thus allowing the user a variety of different options for covering different numbers of holes or portions of holes. In the exemplary embodiment shown in FIG. 10, tab or switch 82 has been moved slightly downwards, thus demonstrating a sealing of the top row of the series of holes 78. Consequently, exhaust gas flow can be greatly varied through positioning of tab or switch 82 on slide 80.

In yet another embodiment of the present invention, a variety of different methods may be used to secure gas delivery tubes to the cannula. In one embodiment, gas delivery tubes may be attached and secured from an above position to a cannula with upward-angled distal ends, as shown, for example, in FIG. 1, items 10 and 12. In another embodiment, gas delivery tubes may be attached and secured from below to a cannula with downward-angled distal ends, as shown, for example, in FIG. 4, items 36 and 38. In either of these embodiments the gas delivery tubes can be attached and secured to the cannula in any manner, for example friction or adhesion.

In another embodiment of the invention, any of the above styles or configurations of an exhaust port or ports may be used on a mask-type ventilation device. In an exemplary embodiment as shown in FIG. 11, a ventilation mask 90 may be disposed over the nose of a user or over the mouth and nose of a user. Mask 90 may have an outer body 92 and a gas or aerosol delivery tube 94. A series of exhaust ports 96 may be disposed on the front of a mask, similar to the series of exhaust ports shown in FIG. 10. Further, tab 98 and slide 100 could be disposed either above or next to the series of exhaust ports. As shown in FIG. 11, tab 98 has been moved slightly down in slide 100, demonstrably showing the first row of exhaust ports 96 as sealed. Tab 98 may be moved anywhere on slide 100, allowing for the size of some of the exhaust ports to be altered to vary exhaust gas flow and optionally sealed, preventing exhaust gas flow. Thus a user may adjust the gas flow to their desired or prescribed setting.

In yet another exemplary embodiment of the present invention, as shown in FIG. 12, a single exhaust port 116 may be disposed on the front portion of a mask 110. Mask 110 may have at least one gas or aerosol delivery tube 112. Exhaust port 116 may be any of a variety of sizes or shapes. In one exemplary embodiment, exhaust port 116 is substantially circular and has a diameter between 8 and 10 mm. Further, as in previous exemplary embodiments, a variety of methods may be utilized to alter the size, shape and appearance of exhaust port 116. In one exemplary embodiment, device 118 incorporates slide 120 and tab 122 which may be disposed above, below or alongside exhaust port 116. In the exemplary embodiment shown in FIG. 12, tab 122 may be moved from left to right, causing walls 124a and 124b, which may be disposed inside outer body 114 of mask 110, to come closer together and optionally fully together, thus decreasing the area through which exhaust gas may flow. In this embodiment, tab 122 may be moved to any position on slide 120, and the open area of exhaust gas port 116 will correlate to the location of the tab, decreasing as tab 122 goes from left to right or, in an alternative embodiment, top to bottom.

In a further embodiment of the invention, plugs may be used to decrease the open diameter of exhaust port 116. In this exemplary embodiment, an open exhaust port having a diameter of, for example, 8-10 mm, may be disposed on the front of ventilation mask 110. A series of plugs may be associated with the mask such that a plug may be inserted into the open exhaust port 116. The plugs may have a generally donut shape and, when inserted into the open exhaust port, decrease the open area of the exhaust port by a predetermined amount, similar to those shown in FIG. 9. In a further exemplary embodiment, the plugs may cause the diameter of the open exhaust port 116 to decrease in 2 mm increments, from 10 mm down to 2 mm, depending on the plug used.

Figure 13:
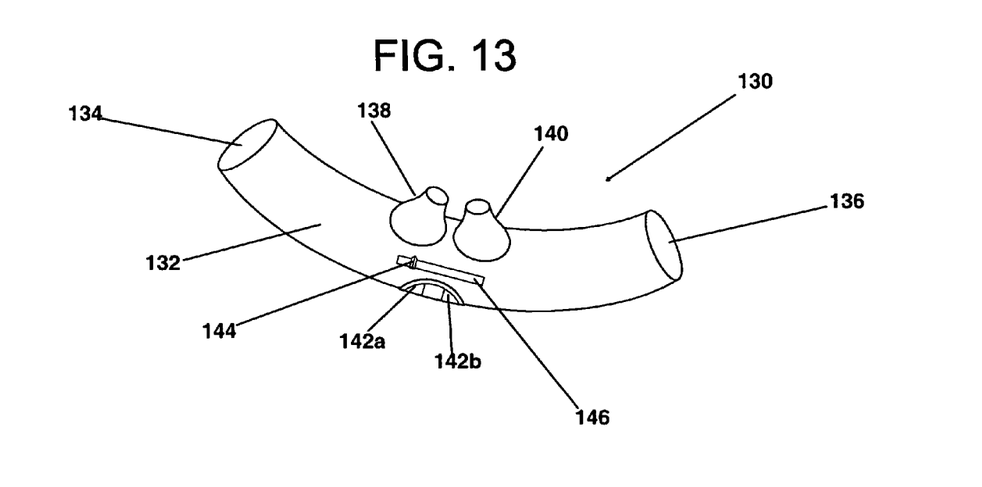
FIG. 13 illustrates another exemplary embodiment of the present invention, showing a cannula designed to curve around the face of a user.
Figure 14:
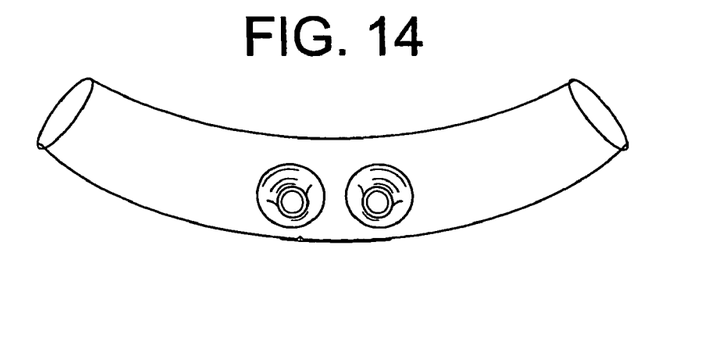
FIG. 14 illustrates a top-down view of the exemplary embodiment shown in FIG. 13.

In another exemplary embodiment, FIG. 13 shows a ventilation interface having a different curvature and FIG. 14 shows a top-down view of the embodiment shown in FIG. 13. Ventilation interface 130 utilizes cannula 132 to provide gas or aerosol from an outside source to a user. Cannula 132 is designed so that it may curve around the face of a user. For example, interface 130 could be worn by a person such that cannula 132 curves under the nose and contours to the upper jaw line of that user. In this embodiment, distal ends 134 and 136 may be connected to gas or aerosol delivery tubes. Nasal inserts 138 and 140 are disposed on the top portion of cannula 132 and act to deliver the gas or aerosol to a user.

Additionally, in a further embodiment of the invention, exhaust port 142 may be disposed on the front portion of cannula 130. Exhaust port 142 may be of any size or shape such as those discussed in previous embodiments. Additionally, a plurality of exhaust ports, as discussed in previous embodiments, may be disposed on the front portion of cannula 132. In a further exemplary embodiment, exhaust port 142 may have an adjustable aperture. As shown in FIG. 13, tab 144 and slide 146 are disposed above exhaust port 142. Tab 144 may be moved from left to right on slide 146 to vary the size of the aperture in exhaust port 142. Tab 144 may be moved to any location on slide 146 in order to achieve the desired exhaust gas flow through cannula 132. In another embodiment of the invention, exhaust port 142 may be moved to the bottom portion of cannula 130 to provide for different exhaust gas flow characteristics. Additionally, tab 144 and slide 146 may be moved to a different position on cannula 132 so as to reflect the movement of exhaust port 142. Additionally, any alternative embodiment of varying the exhaust gas flow may be used in this embodiment of the invention. Further, in another embodiment of the invention, the exhaust port may optionally be located substantially opposite the nasal inserts.

Figure 15:
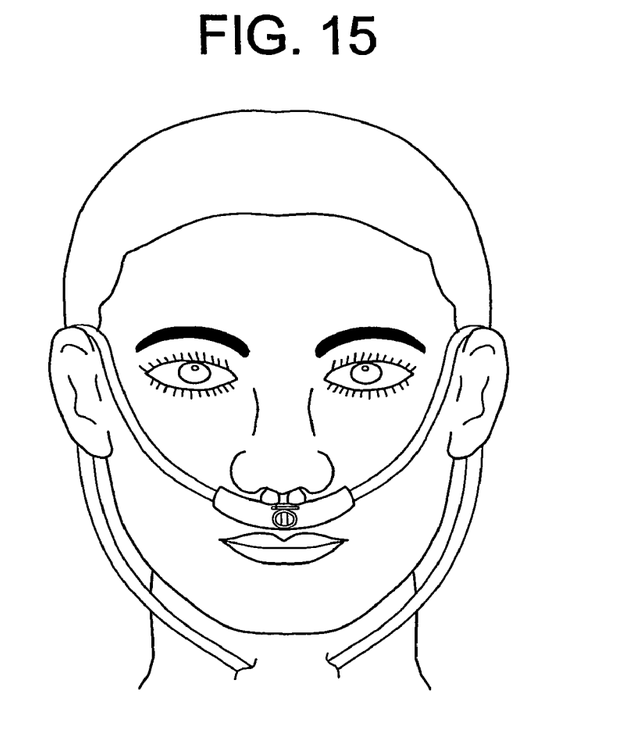
FIG. 15 illustrates an exemplary embodiment of the device shown in FIGS. 13 and 14 being used by a person.

The exemplary embodiment of FIGS. 13 and 14 is shown on the face of a user in FIG. 15. In FIG. 15, ventilation interface 130 is shown with nasal inserts 138 and 140 inserted into the nose of a user. Exhaust port 142 is shown in this embodiment as facing outwards. In another exemplary embodiment of the invention, exhaust port 142 could be positioned on cannula 132 opposite nasal inserts 138 and 140. Additionally, as shown in FIG. 15, tubes 150 and 152 is shown as being connected to distal ends 134 and 136, respectively. The tubes may be inserted into the distal ends and held there through any of a variety of methods, for example friction, flanges, or any other method. The tubes may further allow for the delivery of air, oxygen, aerosolized medication or any of a variety of different gases or medications to ventilation interface 130.

Figures 16A, 16B:
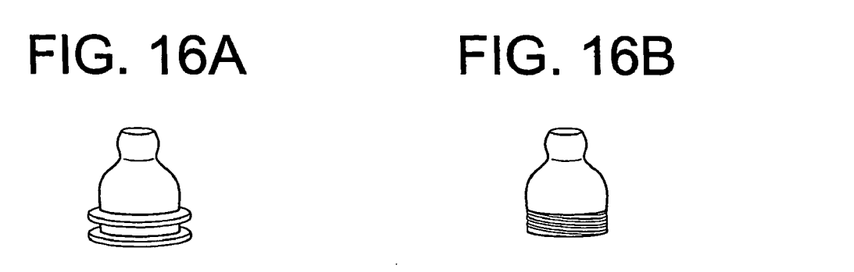
FIG. 16A illustrates exemplary embodiment of the invention showing a detachable nasal insert having a flanged bottom portion.
FIG. 16B illustrates another exemplary embodiment of the invention showing a detachable nasal insert having a threaded bottom portion.

FIGS. 16A and 16B show two exemplary embodiments of detachable nasal inserts. In one embodiment of the invention, the nasal inserts in FIGS. 16A and 16B may be inserted and removed from the cannulae shown in previous embodiments. In another exemplary embodiment, the detachable nasal inserts may be in a variety of forms, such as substantially volcano-shaped, substantially cylindrical or any other shape.

FIG. 16A shows a nasal insert 160 having body 162. On the lower portion of nasal insert 160 is upper flange 164 and lower flange 166. Utilizing the upper and lower flanges, nasal insert 160 may be inserted into a cannula such that an airtight seal may be formed between the cannula, upper flange 164 and lower flange 166.

FIG. 16B shows another exemplary embodiment of a detachable nasal insert. In this embodiment, nasal insert 170 has body 172. At the lower portion of nasal insert 170 is threading 174. In this embodiment, threading 174 may be inserted or screwed into a cannula featuring a receiving threading. When nasal insert 170 is inserted to a cannula, the threading 174 may form an airtight seal between nasal insert 170 and the cannula which it is inserted into.

In a further embodiment of the invention, a variety of techniques may be used to secure the device to the user. In one embodiment, eyes or loops may be disposed on either end of any of the aforementioned cannulae and any type of strap may be threaded through the eyes and adjustably fitted around the head of the user. In another embodiment, latches may be fitted to any of the aforementioned cannulae, allowing a user to attach an adjustable strap. In another exemplary embodiment, as shown in FIG. 15, tubing that may be inserted into the ventilation interface may be configured to fit over the ears of a user, thus further securing the device to the user.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims

What is claimed is:

1. An interface, comprising:
   a cannula having a hollow, arcuate body and a semi-cylindrical bottom wall defining an air chamber, the hollow, arcuate body having cylindrical tubes at opposing ends of the body adapted for connection to gas supply tubes;
   at least one nasal insert having a base end connected to a top wall of the cannula and having an open distal tip end; and
   at least one exhaust port having an adjustable aperture with a cross-sectional area, wherein the cross-sectional area of the aperture is adjustable and wherein the adjustable aperture of the at least one exhaust port is adjusted by moving a tab in a slide that moves a seal a proportional distance over the adjustable aperture of the at least one exhaust port, wherein the slide includes a linear opening defined in the cannula where the tab is adjusted and wherein the linear opening is adjacent to the adjustable aperture;
   the at least one nasal insert being formed in a shape such that it is adapted to be retained in nares of a user through friction and lateral pressure of gas flow.

2. The interface of claim 1, wherein the shape of the cannula is adapted to substantially adhere to contours of a face of a user.

3. The interface of claim 1, wherein the at least one nasal insert has a base area that is larger than an area of the distal tip end and a center area that is smaller than a diameter of the distal tip.

4. The interface of claim 1, wherein the at least one nasal insert has a base area that is larger than an area of a distal tip end.

5. The interface of claim 1, wherein the at least one nasal insert has a distal tip end adapted to substantially contour to an interior of the nares of a user.

6. The interface of claim 1, wherein the at least one nasal insert has a distal tip end that is substantially oval.

7. The interface as in claim 1, wherein the at least one nasal insert has a distal tip end that is substantially circular.

8. The interface of claim 1, wherein the at least one exhaust port further comprises a series of exhaust ports linearly disposed on the cannula substantially opposite the at least one nasal insert.

9. The interface of claim 1, wherein the at least one exhaust port can be at least partially sealed by a covering connected to the cannula.

10. The interface of claim 1, wherein the cannula has at least one opening disposed proximal to each distal end of the cannula.

11. The interface of claim 10, wherein a plug is inserted into the opening disposed proximal to each distal end of the cannula to seal the opening.

12. The interface of claim 1, wherein the adjustable aperture of the at least one exhaust port is adjustably covered by a movable strip of flexible material with several openings disposed theron.

13. The interface of claim 1, wherin a variety of different gaskets are inserted into the at least one exhaust port to alter a size of the aperture.

14. A ventilation interface, comprising:
   an inlet for connection to an input device;
   a central portion adapted to fit over at least a nose of a user for providing gas to the user; and
   at least one exhaust port having an adjustable aperture with a cross-sectional area, wherein the cross-sectional area of the aperture is adjustable, wherein the adjustable aperture of the at least one exhaust port is adjusted by moving a tab in a slide that moves a seal a proportional distance over the adjustable aperture of the at least one exhaust port, wherein the slide includes a linear opening defined in the cannula where the tab is adjusted and wherein the linear opening is adjacent to the adjustable aperture.

15. The ventilation interface of claim 14, wherein the adjustable aperture of the at least one exhaust port is adjusted by inserting a gasket having a smaller aperture into the at least one exhaust port.

16. The ventilation interface of claim 14, wherein the at least one exhaust port comprises a series of exhaust ports.

17. A detachable nasal insert, comprising: a first portion; a second portion having a diameter greater than the first portion; a center portion between the first portion and the second portion, wherein the center portion has a diameter less than the first portion; and a third portion having a first and second flange; and having at least one exhaust port having an adjustable aperture with a cross-sectional area, wherein the cross-sectional area of the aperture is adjustable and wherein the adjustable aperture of the at least one exhaust port is adjusted by moving a tab in a slide that moves a seal a proportional distance over the adjustable aperture of the at least one exhaust port; wherein the slide includes a linear opening defined in the cannula where the tab is adjusted and wherein the linear opening is adjacent to the adjustable aperture.

18. The detachable nasal interface as in claim 17, wherein the first flange is disposed prior to a bottom portion of the detachable nasal insert and the second flange disposed below the first flange.

19. The detachable nasal insert of claim 17, wherein the first and second flange of the third portion are adapted to be inserted into a nasal cannula.

20. The detachable nasal insert of claim 17, wherein the first and second flange of the third portion are adapted to form an airtight seal between the detachable nasal insert and a nasal cannula.

* * * * *